United States Patent
L'Alloret

(10) Patent No.: US 6,878,754 B2
(45) Date of Patent: Apr. 12, 2005

(54) HEAT-INDUCED GELLING FOAMING COMPOSITION AND FOAM OBTAINED

(75) Inventor: Florence L'Alloret, Paris (FR)

(73) Assignee: L'Oreal, Paris (FR)

( * ) Notice: Subject to any disclaimer, the term of this patent is extended or adjusted under 35 U.S.C. 154(b) by 240 days.

(21) Appl. No.: 10/070,922

(22) PCT Filed: Jan. 14, 2002

(86) PCT No.: PCT/FR02/00123
§ 371 (c)(1), (2), (4) Date: Mar. 13, 2002

(87) PCT Pub. No.: WO02/055608
PCT Pub. Date: Jul. 18, 2002

(65) Prior Publication Data
US 2003/0083388 A1 May 1, 2003

(30) Foreign Application Priority Data
Jan. 15, 2001 (FR) .............................. 01 00485

(51) Int. Cl.⁷ ................................................. C08J 9/00
(52) U.S. Cl. .................... 521/134; 521/149; 525/329.7; 525/330.2
(58) Field of Search ................................ 521/134, 149; 525/329.7, 330.2

(56) References Cited

U.S. PATENT DOCUMENTS

| 5,509,913 A | * | 4/1996 | Yeo ............................ 604/364 |
| 5,550,225 A | | 8/1996 | Philippe |
| 5,939,485 A | | 8/1999 | Bromberg et al. |

FOREIGN PATENT DOCUMENTS

| EP | 0 583 814 | 2/1994 |
| EP | 0 629 649 | 12/1994 |
| FR | 2 739 556 | 10/1995 |
| WO | 95/24430 | 9/1995 |
| WO | 97/00275 | 1/1997 |
| WO | 97 05185 | 2/1997 |
| WO | 98 48768 | 11/1998 |
| WO | 98 50005 | 11/1998 |
| WO | 98 51694 | 11/1998 |
| WO | 00 35961 | 6/2000 |

OTHER PUBLICATIONS

D. Hourdet et al.: "Reversible thermothickening of aqueous polymer solutions", Polymer, vol. 35, No. 12, pp. 2624–2630, 1994.
F. L'Alloret et al.: "Aqueous solution behavior of new thermoassociative polymers", Coll. Polym. Sci., vol. 273, No. 12, pp. 1163–1173, 1995.
F. L'Alloret et al.: "Reversible thermoassociation of water-soluble polymers", Revue de l'Institut Francais du Petrole, vol. 52, No. 2, pp. 117–128, 1997.
Lloyd D. Taylor et al.: "Preparation of films exhibiting a balanced temperature dependence to permeation by aqueous solutions—a study of lower consolute behavior", Journal of Polymer Science, vol. 13, pp. 2551–2570, 1975.
F.E. Bailey et al.: "Some properties of poly(ethylene oxide) in aqueous solution", Journal of Applied Polymer Science, vol. 1, No. 1, pp. 56–62, 1959.
M. Heskins et al.: Solution properties of Poly (N-isopropylacrylamide), J. Macromol. Sci—Chem., vol. A2, No. 8, pp. 1441–1455, 12/68.

* cited by examiner

Primary Examiner—Morton Foelak
(74) Attorney, Agent, or Firm—Oblon, Spivak, McClelland, Maier & Neustadt, P.C.

(57) ABSTRACT

Heat-induced gelling foaming composition comprising an aqueous phase, said aqueous phase comprising a polymer comprising water-soluble units and units having in water a lower critical solution temperature LCST, the heat-induced demixing temperature by heating in aqueous solution of said units with an LCST being from 5 to 40° C. for a concentration by mass in water of 1% of said units, and the concentration of said polymer in said composition being such that the gel point is in the range from 5 to 40° C.

Foam obtained from the said foaming composition.

The compositions according to the invention are essentially compositions for topical application and especially cosmetic or dermatological compositions, for example make-up-removing compositions.

38 Claims, No Drawings

HEAT-INDUCED GELLING FOAMING COMPOSITION AND FOAM OBTAINED

The present invention relates to heat-induced gelling foaming compositions, that is to say compositions whose viscosity increases when the temperature increases. The invention also relates to the foam obtained from these foaming compositions and to the use of specific polymers in these foaming compositions.

The compositions and foams according to the invention are essentially compositions for topical application and especially cosmetic or dermatalogical application.

The technical field of the invention may be defined in general as that of foams. Foams are generally dispersions of bubbles of a gas, such as air, in a continuous phase, generally an aqueous phase.

The foaming compositions, formulations or foaming products used, for example in cosmetics, contain foaming surfactants with a concentration of from 5 to 20% by mass. However, the surfactants used in foaming products, which are amphiphilic species of low molar mass, i.e. less than 2 000 g/mol, have the drawback of having a relatively aggressive nature with respect to the skin. In addition, these products or compositions or formulations, which are generally in fluid or gelled form at room temperature, have numerous limitations regarding their use. Specifically:

the fluid formulations are difficult to apply on account of their low viscosity, leading to them running when applied;

the gelled formulations are obtained using hydrophilic gelling agents, such as crosslinked poly-acrylic acids, in particular the derivatives sold under the name Carbopol®, which limit the type of presentation form obtained.

In addition, generally, the phase of initiation of the foam for the gelled formulations is slower than for products not containing a gelling agent, and the formulation applied to the skin, after dilution with water, has a low viscosity.

In other words, if it is desired at the present time to provide a gelled foam on the skin, use must necessarily be made of a foaming composition which is itself gelled, with all the attendant drawbacks. The variety of textures, that may be provided by a foaming composition capable of giving a gelled foam when applied to the skin, is thus extremely limited.

There is thus a need for a foaming composition which is relatively nonaggressive for the skin, which has considerable foaming properties, especially when applied to the skin and/or in the presence of warm water, for example from 30 to 40° C., which gives stable foams, and finally, which can take on many textures combined with an easy application.

The aim of the present invention is, inter alia, to satisfy this need.

This aim and others are achieved, in accordance with the invention, by a heat-induced gelling foaming composition comprising an aqueous phase, said aqueous phase comprising a polymer comprising water-soluble units and units having in water a lower critical solution temperature LCST, the demixing temperature by heating in aqueous solution of said units with an LCST being from 5 to 40° C. for a concentration of said units in water of 1% by mass, and the concentration of said polymer in said composition being such that its gel point is in the range from 5 to 40° C.

Surprisingly, it has been shown that the foaming compositions according to the invention, which comprise the specific polymer as defined above, at the specific concentration defined above, make it possible to satisfy the needs listed above and to satisfy all the requirements mentioned in the text hereinabove. Especially, the polymer makes it possible to obtain a composition which gels when applied and gives a stable foam.

In addition, the foaming compositions according to the invention can optionally comprise little or no surfactants.

Accordingly, the compositions or foaming formulations according to the invention have a very good level of harmlessness with respect to the skin.

The foaming compositions according to the invention have considerable foaming properties and produce a stable foam, especially above 30° C. and possibly in the presence of warm water.

The foaming compositions according to the invention may be in any form at a temperature that is below their gel point, for example at room temperature.

That is to say that at a temperature below their gel point, for example at room temperature, the compositions of the invention may have a low or else a high viscosity. This means that "in the jar", that is to say prior to an increase in temperature generally occurring at the moment they are used, for example when they are applied, generally to the skin, and to the formation of foam likewise generally occurring at the moment of this use, the range of textures accessible by the compositions of the invention is not limited.

In contrast, the analogous compositions of the prior art can provide only an extremely limited number of textures and must necessarily be in gelled form, if it is desired to obtain a gel, for example during the application and the concomitant formation of the foam.

According to the invention, there is no restriction on the form of the composition at room temperature.

The form of the foaming composition may be varied as desired, and yet, irrespective of this form, when it is applied, for example to the skin (the temperature of which is generally in the region of 32° C.) which is accompanied by an increase in temperature, the gelling power of the polymer will appear and gelation will occur, with formation of a stable and long-lasting foam. By virtue of the gelation, this texture is easy and pleasant to apply.

Furthermore, it has been found that the polymers included in the foaming composition of the invention do not "kill" the foam, unlike the gelling polymers of the prior art, and that the said foam is stable for a long time.

In other words, the foaming compositions according to the invention are, for example, in fluid form at room temperature, and their viscosity becomes large at a higher temperature, which is that encountered, for example, during application to the skin. Such a gelation, brought about at the temperature of the skin, generally in the region of 32° C., allows an easy application of the compositions or formulations according to the invention. The phenomenon of gelation may also be reinforced in the presence of warm water, generally at a temperature of 30 to 40° C.

The invention also relates to the foam which may be obtained from the foaming composition described above, this foam being formed from a dispersion of gas bubbles in the continuous aqueous phase. This foam has all the properties inherent in the use of the specific polymer described above, namely, essentially the fact that the foam obtained is stable above the gel point, for example the temperature of application especially to the skin.

The invention relates to the use of the polymer as described in the present invention to stabilize a foam at a temperature above its gel point.

The invention also relates to the cosmetic use of a composition according to the invention, for cleansing and/or removing make-up from the skin, the scalp, the nails, the eyelashes, the eyebrows, the eyes, mucous membranes, semi-mucous membranes and/or the hair.

Finally, the invention relates to a cosmetic process for cleansing and/or removing make-up from keratin materials (skin, scalp, nails, eyelashes, eyebrows, eyes, mucous membranes, semi-mucous membranes and/or hair), characterized in that the composition of the invention is applied to the keratin materials, in the presence of water, and the foam formed and the soiling residues are removed by rinsing with water.

The essential constituent of the compositions according to the invention is a polymer comprising water-soluble units and units having in water a lower critical solution temperature (LCST), also known as "Units with an LCST".

In this respect, it is useful to recall that the expression "units with an LCST" means units whose solubility in water is modified beyond a certain temperature. These are units with a heat-induced demixing temperature (or cloud point) defining their region of solubility in water. The minimum demixing temperature obtained as a function of the concentration of polymer consisting solely of units with an LCST is known as the "LCST" (Lower Critical Solution Temperature). For each concentration of LCST polymer, a heat-induced demixing temperature (or demixing temperature by heating) is observed. It is higher than the LCST, which is the minimum point of the curve. Below this temperature, the polymer is soluble in water, and above this temperature, the polymer loses its solubility in water.

These units with an LCST of the polymer used in the foaming composition according to the invention correspond to a specific definition which, fundamentally, makes it possible to communicate to the polymer comprising them the advantageous heat-induced gelling properties described above.

These units with an LCST of the polymer have, according to the invention, a heat-induced demixing temperature of from 5 to 40° C. for a concentration by mass in water of 1% by weight of the said units with an LCST.

Preferably, the heat-induced demixing temperature in aqueous solution of the units with an LCST of the polymer is from 10 to 35° C. for a concentration by mass in water of 1% of the said units with an LCST.

Preferably, the polymer concentration is such that the gel point is in the range from 10 to 35° C.

The polymer having the structure described above with water-soluble units and specific units with an LCST defined above has in aqueous solution gelation properties beyond a critical temperature, or heat-induced gelling properties.

These heat-induced gelling properties observed beyond the demixing temperature of the LCST chains are described in the prior art, especially in documents [1], [2] and [3]. They are due to the combination of the LCST chains within hydrophobic microdomains beyond their demixing temperature, thus forming crosslinking nodes between the main chains.

These gelling properties are observed when the polymer concentration is sufficient to allow interactions between LCST grafts borne by different macromolecules. The minimum concentration required, known as the "critical aggregation concentration", or CAC, is evaluated by rheological measurements: it is the concentration at and above which the viscosity of an aqueous solution of the polymers of the invention becomes higher than the viscosity of a solution of the equivalent polymer not comprising LCST chains.

Beyond the CAC, the polymers of the invention have gelling properties when the temperature becomes higher than a critical value, known as the "gel point", or $T_{gel}$.

According to the literature data, there is good agreement between $T_{gel}$ and the demixing temperature of the LCST chains, under the same concentration conditions. The gel point of an aqueous solution of a polymer of the invention is determined by rheological measurements: it is the temperature at and above which the viscosity of a solution of a polymer of the invention becomes higher than the viscosity of a solution of the equivalent polymer not comprising LCST chains.

The polymers of the invention are characterized by a specific gel point generally of from 5 to 40° C., preferably from 10 to 35° C., for a concentration by mass in water equal to, for example, 2% by weight.

This specific gel point allows these polymers to give the compositions of the invention all the advantageous properties mentioned above, and in particular their wide variety of forms at room temperature, and their gelled foam texture effect when applied.

Polymers comprising, in the manner of those used in the compositions of the invention, water-soluble units and units with an LCST and having heat-induced gelling properties observed above the demixing temperature of the LCST chains are described in the documents already mentioned above.

Document [1] relates to the reversible heat-induced thickening of aqueous solutions of copolymers comprising a water-soluble backbone of polyacrylic acid with poly (ethylene oxide) (PEO) grafts.

Document [2] relates to the heat-induced thickening behaviour in aqueous solution of polymers comprising a 2-acrylamido-2-methylpropanesulphonic acid (AMPS) backbone and poly(ethylene oxide) side chains.

Similarly, document [3] describes the reversible heat-induced association of copolymers with a polyacrylic water-soluble backbone or based on AMPS with PEO grafts.

Polymers, such as those mentioned in documents [1], [2] and [3], find their use in particular in the petroleum industry.

Thus, document [4] describes thermoviscosifying polymers with a water-soluble backbone comprising segments with an LCST, or bearing side chains with an LCST, which may be used especially as thickeners, constituents of drilling fluids or other fluids, and industrial cleaning fluids.

Document [5] describes polymers similar to those of document [4] and their use as anti-sedimentation agents for suspensions, possibly in cosmetic preparations.

It should be noted that none of the documents [1] to [5] mentions the incorporation of polymers into foaming compositions and that, in addition, the polymers described do not comprise the specific units with an LCST according to the invention.

Document [6] also describes copolymers comprising a backbone consisting of pH-sensitive units, for example polyacrylic units, and heat-sensitive units, grafted onto this backbone. These copolymers have heat-induced gelling properties and they are used for the liberation and controlled release of active principles or pharmaceutical agents, and possibly cosmetic agents, by topical application.

The heat-sensitive units in the copolymers of this document are not the specific units with an LCST of the polymers of the invention. Furthermore, the polymers according to document [6] are characterized by the extremely inconvenient opacity of the heat-induced products, which is not the case for the polymers used in the foaming compositions of the invention.

In point of fact, the polymer in said document is fundamentally different from that of the invention since it has overall for the entire polymer an LCST in the temperature range from 20 to 40° C., rather than a gel point.

Documents [7] and [8] describe reversible-gelling polymer systems, comprising a sensitive component capable of aggregation, in response to a change in an external "stimulus", and a structural component. The external stimulus may be, for example, the temperature.

The component that is sensitive to the external stimulus is fundamentally different from the units with an LCST of the application. Specifically, these components that are sensitive to the external stimulus in fact consist of at least one hydrophilic fragment and one hydrophobic fragment. Thus, the sensitive component may be a block copolymer, such as a "poloxamer", for example a Pluronic®, which is a block polymer of ethylene oxide (soluble) and of propylene oxide (insoluble); such a block copolymer aggregates microscopically beyond a critical temperature not corresponding to an LCST. A nonionic surfactant may also be used as sensitive component.

Document [7] relates more particularly to a polymer network formed from a water-soluble polyacrylic backbone and a Pluronic® sensitive component, which is interlocked in the said backbone, without covalent bonding; this network thus has a particular structure that has nothing in common with the polymer of the invention. On the other hand, in document [8], it is a matter of polymers with covalent bonds.

These polymers have heat-induced gelling properties and they may be used in the pharmaceutical field for the delivery of medicinal products and in many other fields, including the cosmetics field. As regards the cited cosmetic applications, only examples of emulsions are mentioned. They all contain a neutral, anionic or cationic surfactant, along with the polymer acting as gelling agent.

The use of the polymers in foams is never mentioned, nor are the stabilizing and texture effects obtained in the invention.

In these formulations, the sensitive component of the polymer system has a behaviour that is different from that of the units with an LCST, such as those of the polymer of the invention, during heating. Thus, when the said sensitive component (for example poloxamer) is heated to about 30–40° C., it shows a temperature of micellization, that is to say an aggregation at the microscopic level, and then, when it is heated further, an LCST temperature that is very much higher. This LCST corresponds to an aggregation at the macroscopic level between the macromolecules. It is explained in WO-A-97/00275 [8] on pages 16 and 17 that the gelation and the LCST are observed at temperatures which differ by about 70° C., the gel point corresponding to the micellization temperature of the sensitive component, which shows that these polymers are different from those of our application. In addition, it is not possible, on account of the synthesis used in document [8], to fully control the structure and properties of the final polymer obtained, as is the case in the compositions of the invention.

Cosmetic compositions using a reversible heat-induced gelling polymer system, comprising polyacrylic acid and a poloxamer as in documents [7] and [8], are also known from document [9]. Once again, the polymer system of these documents is fundamentally different from those used in the compositions of the invention, to the point that the advantageous properties of the compositions of the invention cannot be obtained.

WO-A-00/35961 [10] describes the preparation of polymers with heat-induced thickening properties by emulsion polymerization and the use of these polymers in pharmaceutical and cosmetic compositions. These polymers may be copolymers containing water-soluble units and units with an LCST based on alkylene oxide. It is envisaged to add nonionic surfactants to the polymers to reinforce their heat-induced thickening properties.

It emerges from the foregoing text that the use in foaming compositions of the polymers according to the invention, containing specific units with an LCST and specific gel points giving them heat-induced foam-stabilizing properties and a gelling texture effect when applied, is neither described nor suggested in the documents of the prior art.

The polymers used in the invention may be block polymers or grafted polymers, which comprise, on the one hand, water-soluble units, and on the other hand, units with an LCST as defined above.

It is pointed out that, in the present text, the water-soluble units or the units with an LCST of the polymers used according to the invention are defined as not including the groups linking together, on the one hand, the said water-soluble units and, on the other hand, the said units with an LCST.

The said linking groups are derived from the reaction, during the preparation of the polymer, of the reactive sites borne, on the one hand, by the precursors of the said water-soluble units and, on the other hand, by the precursors of the said units with an LCST.

The polymers used in the context of the invention may thus be block polymers comprising, for example, blocks consisting of water-soluble units alternating with blocks with an LCST.

These polymers may also be in the form of grafted polymers whose backbone is formed by water-soluble units, the said backbone bearing grafts consisting of units with an LCST.

The said polymers may be partially crosslinked.

The expression "water-soluble units" generally means that these units are units that are soluble in water, at a temperature of from 5 to 80° C., in a proportion of at least 10 g/l and preferably of at least 20 g/l.

However, the expression "water-soluble units" also means units not necessarily having the solubility mentioned above, but which, in aqueous solution at 1% by weight, from 5 to 80° C., allow the production of a macroscopically homogeneous and transparent solution, that is to say a solution having a maximum light transmittance value, irrespective of the wavelength, of between 400 and 800 nm, through a sample 1 cm thick, of at least 85% and preferably of at least 90%.

These water-soluble units do not have a heat-induced demixing temperature of LCST type.

These water-soluble units are totally or partially capable of being obtained by polymerization, especially free-radical polymerization, or by polycondensation, or alternatively consist totally or partially of existing natural polymers or modified natural polymers.

By way of example, the water-soluble units are totally or partially capable of being obtained by polymerization, especially free-radical polymerization, of at least one monomer chosen from the following monomers:

(meth)acrylic acid;
vinyl monomers of formula (I) below:

in which:
R is chosen from H, —CH$_3$, —C$_2$H$_5$ or —C$_3$H$_7$; and
X is chosen from:

alkyl oxides of —OR' type in which R' is a linear or branched, saturated or unsaturated hydrocarbon-based radical containing from 1 to 6 carbon atoms, optionally substituted with at least one halogen atom (iodine, bromine, chlorine or fluorine); a sulphonic (—$SO_3^-$), sulphate (—$SO_4^-$), phosphate (—$PO_4H_2$); hydroxyl (—OH); primary amine (—$NH_2$); secondary amine (—$NHR_1$), tertiary amine (—$NR_1R_2$) or quaternary amine (-$N^+R_1R_2R_3$) group with $R_1$, $R_2$ and $R_3$ being, independently of each other, a linear or branched, saturated or unsaturated hydrocarbon radical containing 1 to 6 carbon atoms, with the proviso that the sum of the carbon atoms of $R'+R_1+R_2+R_3$ does not exceed 7; and —$NH_2$, —$NHR_4$ and —$NR_4R_5$ groups in which $R_4$ and $R_5$ are, independently of each other, linear or branched, saturated or unsaturated hydrocarbon-based radicals containing 1 to 6 carbon atoms, with the proviso that the total number of carbon atoms of $R_4+R_5$ does not exceed 7, the said $R_4$ and $R_5$ optionally being substituted with a halogen atom (iodine, bromine, chlorine or fluorine); a hydroxyl (—OH); sulphonic (—$SO_3^-$); sulphate (—$SO_4^-$); phosphate (—$PO_4H_2$); primary amine (—$NH_2$); secondary amine (—$NHR_1$), tertiary amine (—$NR_1R_2$) and/or quaternary amine (—$N^+R_1R_2R_3$) group with $R_1$, $R_2$ and $R_3$ being, independently of each other, a linear or branched, saturated or unsaturated hydrocarbon radical containing 1 to 6 carbon atoms, with the proviso that the sum of the carbon atoms of $R_4+R_5+R_1+R_2+R_3$ does not exceed 7;

maleic anhydride;

itaconic acid;

vinyl alcohol of formula $CH_2$=CHOH;

vinyl acetate of formula $CH_2$=CH—$OCOCH_3$;

N-vinyllactams such as N-vinylpyrrolidone, N-vinylcaprolactam and N-butyrolactam;

vinyl ethers of formula $CH_2$=$CHOR_6$ in which $R_6$ is a linear or branched, saturated or unsaturated hydrocarbon radical containing from 1 to 6 carbons;

water-soluble styrene derivatives, especially styrene sulphonate;

dimethyldiallylammonium chloride; and vinylacetamide.

The polycondensates and natural polymers or modified natural polymers which may constitute all or part of the water-soluble units are chosen from one or more of the following components:

water-soluble polyurethanes, xanthan gum, especially the product sold under the names Keltrol T and Keltrol SF by Kelco; or Rhodigel SM and Rhodigel 200 from Rhodia;

alginates (Kelcosol from Monsanto) and derivatives thereof such as propylene glycol alginate (Kelcoloid LVF from Kelco);

cellulose derivatives and especially carboxymethylcellulose (Aquasorb A500, Hercules), hydroxypropylcellulose, hydroxyethylcellulose and quaternized hydroxyethylcellulose;

galactomannans and derivatives thereof, such as Konjac gum, guar gum, hydroxypropylguar, hydroxypropylguar modified with sodium methylcarboxylate groups (Jaguar XC97-1, Rhodia), hydroxypropyltrimethylammonium guar chloride.

Mention may also be made of polyethyleneimine.

The water-soluble units preferably have a molar mass ranging from 1000 g/mol to 5 000 000 g/mol when they constitute the water-soluble backbone of a grafted polymer.

These water-soluble units preferably have a molar mass ranging from 500 g/mol to 100 000 g/mol when they constitute a block of a multiblock polymer.

The units with an LCST of the polymers used in the invention may be defined as being units whose water solubility is modified beyond a certain temperature. They are units with a heat-induced demixing temperature (or cloud point) defining their region of solubility in water. The minimum demixing temperature obtained as a function of the polymer concentration is referred to as the "LCST" (Lower Critical Solution Temperature). For each polymer concentration, a heat-induced demixing temperature is observed; it is higher than the LCST, which is the minimum point of the curve. Below this temperature, the polymer constituting the unit with an LCST is soluble in water; above this temperature, the polymer constituting the unit with an LCST loses its solubility in water.

Some of these polymers with an LCST are especially described in the articles by Taylor et al., Journal of Polymer Science, part A: Polymer Chemistry, 1975, 13, 2 551 [11]; by J. Bailey et al., Journal of Applied Polymer Science, 1959, 1,56 [12]; and by Heskins et al., Journal of Macromolecular Science, Chemistry A2, 1968, vol. 8, 1 441 [13].

The expression "soluble in water at a temperature T" means that the units have a solubility at T of at least 1 g/l and preferably of at least 2 g/l.

The measurement of the LCST may be performed visually: the temperature at which the cloud point of the aqueous solution appears is determined; this cloud point is reflected by the opacification of the solution, or loss of transparency.

In general, a transparent composition will have a maximum light transmittance value, irrespective of the wavelength of between 400 and 800 nm, through a sample 1 cm thick, of at least 85% and preferably of at least 90%.

The transmittance may be measured by placing a sample 1 cm thick in the light beam of a spectrophotometer working in the wavelengths of the light spectrum.

The units with an LCST of the polymers used in the invention may consist of one or more polymers chosen from the following polymers:

polyethers such as polyethylene oxide (PEO), polypropylene oxide (PPO) or random copolymers of ethylene oxide (EO) and of propylene oxide (PO), polyvinyl methyl ethers, polymeric and copolymeric N-substituted acrylamide derivatives with an LCST, such as poly-N-isopropylacrylamide (Nipam) and poly-N-ethylacrylamide, and polyvinylcaprolactam and vinylcaprolactam copolymers.

Preferably, the units with an LCST consist of polypropylene oxide $(PPO)_n$ with n being an integer from 10 to 50, or of random copolymers of ethylene oxide (EO) and of propylene oxide (PO), represented by the formula:

$(EO)_m(PO)_n$ in which m is an integer ranging from 1 to 40 and preferably from 2 to 20, and n is an integer ranging from 10 to 60 and preferably from 20 to 50.

Preferably, the molar mass of these units with an LCST is from 500 to 5300 g/mol and more preferably from 1500 to 4000 g/mol.

It has been found that the random distribution of the EO and PO units is reflected by the existence of a lower critical solution (demixing) temperature, beyond which a macroscopic phase separation is observed. This behaviour is different from that of the block (EO) (PO) copolymers, which form micelles beyond a critical temperature known as the micellization temperature (microscopic level aggregation).

The units with an LCST may thus especially be amino, especially monoamino, diamino or triamino, random copolymers of ethylene oxide and of propylene oxide. These polymers, before reaction, bear reactive sites, in this case of amine groups, reacting with the reactive sites of the water-soluble polymers, for example carboxyl groups, to give the final polymer used in the invention. In the final polymer, the water-soluble units are linked to the units with an LCST via linking groups derived from the reaction of the reactive sites or groups borne, respectively, by the units with an LCST and the precursors of the water-soluble units. These linking groups will be, for example, amide, ester, ether or urethane groups.

Among the commercially available units with an LCST that may be mentioned are the copolymers sold under the name Jeffamine by Huntsman, and especially Jeffamine XTJ-507 (M-2005), Jeffamine B-2000 and Jeffamine XTJ-509 (or T-3000).

The units with an LCST may also be derived from random EO/PO copolymers containing OH end groups, such as those sold under the name Polyglycols P41 and B11 by Clariant.

Polymeric and copolymeric N-substituted acrylamide derivatives having an LCST, and also polyvinylcaprolactam and vinyl caprolactam copolymers may also be used in the invention as units with an LCST.

As examples of polymeric N-substituted acrylamide derivatives having an LCST, mention may be made of poly-N-isopropylacrylamide, poly-N-ethyl-acrylamide and copolymers of N-isopropylacrylamide (or of N-ethylacrylamide) and of a vinyl monomer chosen from monomers having the formula (I) given above, maleic anhydride, itaconic acid, vinylpyrrolidone, styrene and its derivatives, dimethyldiallylammonium chloride, vinylacetamide, vinyl ethers and vinyl acetate derivatives.

The molar mass of these polymers is preferably from 1000 g/mol to 500 000 g/mol and preferably from 2000 to 50 000 g/mol.

These polymers may be synthesized by free-radical polymerization using a pair of initiators such as aminoethanethiol hydrochloride, in the presence of potassium persulphate, so as to obtain units with an LCST with a reactive amino end group.

As examples of vinylcaprolactam copolymers, mention may be made of copolymers of vinylcaprolactam and of a vinyl monomer having the formula (I) given above, or of a monomer chosen from maleic anhydride, itaconic acid, vinylpyrrolidone, styrene and its derivatives, dimethyldiallylammonium chloride, vinylacetamide, vinyl alcohol, vinyl acetate, vinyl ethers and vinyl acetate derivatives.

The molar mass of these vinylcaprolactam polymers or copolymers is generally from 1000 g/mol to 500 000 g/mol and preferably from 2000 to 50 000 g/mol.

These compounds may be synthesized by free-radical polymerization using a pair of initiators such as aminoethanethiol hydrochloride, in the presence of potassium persulphate, so as to obtain units with an LCST having a reactive amino end group.

The proportion by mass of units with an LCST in the final polymer is preferably from 5% to 70%, especially from 20% to 65% and particularly from 30% to 60% by weight relative to the final polymer.

As seen above, the heat-induced demixing temperature of the said units with an LCST of the polymer used in the invention is from 5 to 40° C. and preferably from 10 to 35° C., for a concentration by mass in water of 1% by weight of the said units with an LCST.

The polymers used in the context of the invention may be readily prepared by a person skilled in the art on the basis of his general knowledge, using grafting, copolymerization or coupling reaction processes.

When the final polymer is in the form of a grafted polymer, especially having a water-soluble backbone with LCST side chains or grafts, it is possible to prepare it by grafting units with an LCST having at least one reactive end group or reactive site, especially an aminated end group or reactive site, onto a water-soluble polymer forming the backbone, bearing at least 10% (on a molar basis) of reactive groups such as carboxylic acid functions. This reaction may be carried out in the presence of a carbodiimide such as dicyclohexylcarbodiimide or 1-(3-dimethylaminopropyl)-3-ethylcarbodiimide hydrochloride, in a solvent such as N-methylpyrrolidone or water.

Another possibility for preparing grafted polymers consists in copolymerizing, for example, a macromonomer with an LCST (chain with an LCST described above with a vinyl end group) and a water-soluble vinyl monomer such as acrylic acid or vinyl monomers having the formula (I).

When the final polymer is in the form of a block polymer, it is possible to prepare it by coupling between water-soluble units and units with an LCST, these units having complementary reactive sites at each end.

In the case of grafting processes and coupling processes, the reactive sites of the units with an LCST may be amine functions, especially monoamines, diamines or triamines, and OH functions. In this case, the reactive sites of the water-soluble units may be carboxylic acid functions. The groups linking the water-soluble units and the units with an LCST will thus be, for example, amide groups or ester groups.

As has been seen previously, the foaming compositions of the invention essentially comprise a continuous aqueous phase.

According to the invention, the aqueous phase comprises a polymer comprising water-soluble units and units with an LCST, as defined above.

Generally, the concentration by mass of polymer of the aqueous phase is from 0.1 to 20% and preferably from 0.5 to 10%.

By virtue of the presence of the specific polymer described above, the foaming composition according to the invention can optionally comprise no surfactant, that is to say that it can be free of surfactant or can contain only a small amount thereof, for example at a concentration by mass of less than or equal to 5% and preferably from 1 to 5%.

However, depending on the final use, the composition of the invention may contain up to 20% by weight of surfactants, for example from 0.05 to 20% and better still from 0.1 to 15% by weight relative to the total weight of the composition.

The foaming surfactants used may be nonionic, anionic, amphoteric or zwitterionic surfactants, nonionic surfactants being preferred.

Nonionic surfactants that may be mentioned, for example, are alkylpolyglycosides (APG), esters of polyols and of fatty acids, esters of polyethylene glycols and of fatty acid, derivatives of fatty alcohols and of polyols (ethers), and oxyalkylenated (oxyethylenated and/or oxypropylenated) derivatives of these compounds. Mention may also be made of maltose esters, polyglycerolated fatty alcohols, glucamine derivatives, for instance 2-ethylhexyloxycarbonyl-N-methylglucamine, and mixtures thereof.

Alkylpolyglucosides which may be mentioned, for example, are decylglucoside (Alkyl-C9/C11-polyglucoside (1.4)), for instance the product sold under the name Mydol 10 by the company Kao Chemicals, the product sold under the name Plantaren 2000 UP and Plantacare 2000 UP by the company Henkel, and the product sold under the name Oramix NS 10 by the company SEPPIC; caprylyl/capryl glucoside, for instance the product sold under the name Oramix CG 110 by the company SEPPIC or under the name Lutensol GD 70 by the company BASF; laurylglucoside, for instance the products sold under the names Plantaren 1200 N and Plantacare 1200 by the company Henkel; and cocoglucoside, for instance the product sold under the name Plantacare 818/UP by the company Henkel, and mixtures thereof.

The maltose derivatives are, for example, those described in document EP-A-0 566 438 [14], such as O-octanoyl-6'-D-maltose or O-dodecanoyl-6'-D-maltose described in document FR-A-2 739 566 [15].

Among the polyglycerolated fatty alcohols that may be mentioned are polyglycerolated dodecanediol (3.5 mol of glycerol), this product being sold under the name Chimexane NF by the company Chimex.

Anionic surfactants which may be used, for example, are carboxylates, amino acid derivatives, alkyl sulphates, alkyl ether sulphates, sulphonates, isethionates, taurates, sulphosuccinates, alkyl sulphoacetates, phosphates and alkyl phosphates, polypeptides, anionic derivatives of alkyl polyglucoside, fatty acid soaps, and mixtures thereof.

Carboxylates which may be mentioned, for example, are alkali metal salts of N-acylamino acids; amidoether carboxylates (AEC), for instance sodium lauryl amidoether carboxylate (3 EO) sold under the name Akypo Foam 30 by the company Kao Chemicals; polyoxyethylenated carboxylic acid salts, for instance oxyethylenated (6 EO) sodium lauryl ether carboxylate (65/25/10 C12-14-16) sold under the name Akypo Soft 45 NV by the company Kao Chemicals; polyoxyethylenated fatty acids of olive oil and of carboxymethyl, for instance the product sold under the name Olivem 400 by the company Biologia E Tecnologia; oxyethylenated (6 EO) sodium tridecyl ether carboxylate sold under the name Nikkol ECTD-6NEX by the company Nikkol; sodium 2-(2-hydroxyalkyloxy)acetate sold under the name Beaulight SHAA by the company Sanyo.

The amino acid derivatives may be chosen, for example, from sarcosinates and especially acyl sarcosinates, for instance sodium lauroyl sarcosinate sold under the name Sarkosyl NL 97 by the company Ciba or sold under the name Oramix L 30 by the company SEPPIC, sodium myristoyl sarcosinate, sold under the name Nikkol Sarcosinate MN by the company Nikkol, sodium palmitoyl sarcosinate, sold under the name Nikkol Sarcosinate PN by the company Nikkol; alaninates, for instance sodium lauroyl-N-methylamidopropionate sold under the name Sodium Nikkol Alaninate LN 30 by the company Nikkol or sold under the name Alanone Ale by the company Kawaken, and triethanolamine N-lauroyl-N-methylalanine, sold under the name Alanone Alta by the company Kawaken; N-acylglutamates, for instance triethanolamine monococoylglutamate sold under the name Acylglutamate CT-12 by the company Ajinomoto, triethanolamine lauroyl glutamate sold under the name Acylglutamate CT-12 by the company Ajinomoto and monosodium N-lauroyl-L-glutamate sold under the name Amisoft LS-11 by the company Ajinomoto; aspartates, for instance the mixture of triethanolamine N-lauroylaspartate and triethanolamine N-myristoylaspartate, sold under the name Asparack LM-TS2 by the company Mitsubishi; citrates, and mixtures thereof.

Glycine derivatives that may be mentioned are sodium N-cocoylglycinate and potassium N-cocoylglycinate, for instance the products sold under the names Amilite GCS-12 and Amilite GCK-12 by the company Ajinomoto.

Alkyl ether sulphates that may be mentioned, for example, are sodium lauryl ether sulphate (70/30 C12-14) (2.2 EO) sold under the names Sipon AOS 225 or Texapon N702 Pate by the company Henkel, ammonium lauryl ether sulphate (70/30 C12-14) (3 EO) sold under the name Sipon LEA 370 by the company Henkel, and ammonium (C12–C14)alkyl ether (9 EO) sulphate sold under the name Rhodapex AB/20 by the company Rhodia Chimie.

Sulphonates that may be mentioned, for example, are α-olefin sulphonates, for instance sodium α-olefin sulphonate (C14-16) sold under the name Bio-Terge AS-40 by the company Stepan, sold under the names Witconate AOS Protégé and Sulframine AOS PH 12 by the company Witco or sold under the name Bio-Terge AS-40 CG by the company Stepan, secondary sodium olefin sulphonate sold under the name Hostapur SAS 30 by the company Clariant; linear alkyl aryl sulphonates, for instance sodium xylene sulphonate sold under the names Manrosol SXS30, Manrosol SXS40 and Manrosol SXS93 by the company Manro.

Isethionates that may be mentioned are acylisethionates, for instance sodium cocoylisethionate, such as the product sold under the name Jordapon CI P by the company Jordan.

Taurates that may be mentioned are the sodium salt of palm kernel oil methyl taurate sold under the name Hostapon CT Pate by the company Clariant; N-acyl N-methyltaurates, for instance sodium N-cocoyl N-methyltaurate sold under the name Hostapon LT-SF by the company Clariant or sold under the name Nikkol CMT-30-T by the company Nikkol, and sodium palmitoyl methyltaurate sold under the name Nikkol PMT by the company Nikkol.

Sulphosuccinates that may be mentioned, for example, are oxyethylenated (3 EO) lauryl monosulphosuccinate (70/30 C12/C14) sold under the names Setacin 103 Special, Rewopol SB-FA 30 K 4 by the company Witco, the disodium salt of a C12–C14 alkyl hemisulphosuccinate, sold under the name Setacin F Special Paste by the company Zschimmer Schwarz, oxyethylenated (2 EO) disodium oleamidosulphosuccinate sold under the name Standapol SH 135 by the company Henkel, oxyethylenated (5 EO) lauramide monosulphosuccinate sold under the name Lebon A-5000 by the company Sanyo, the disodium salt of oxyethylenated (10 EO) lauryl citrate monosulphosuccinate sold under the name Rewopol SB CS 50 by the company Witco, and ricinoleic monoethanolamide monosulphosuccinate sold under the name Rewoderm S 1333 by the company Witco.

Phosphates and alkyl phosphates that may be mentioned, for example, are monoalkyl phosphates and dialkyl phosphates, such as lauryl monophosphate sold under the name MAP 20 by the company Kao Chemicals, the potassium salt of dodecylphosphoric acid, as a mixture of monoester and diester (predominantly diester) sold under the name Crafol AP-31 by the company Cognis, the mixture of monoester and diester of octylphosphoric acid, sold under the name Crafol AP-20 by the company Cognis, the mixture of ethoxylated (7 mol of EO) 2-butyloctanol monoester and diester of phosphoric acid, sold under the name Isofol 12 7 EO-Phosphate Ester by the company Condea, the potassium or triethanolamine salt of mono(C12–C13)alkyl phosphate sold under the references Arlatone MAP 230K-40 and Arlatone MAP 230T-60 by the company Uniqema, and potassium lauryl phosphate sold under the name Dermalcare MAP XC-99/09 by the company Rhodia Chimie.

The polypeptides are obtained, for example, by condensing a fatty chain onto the amino acids of cereals and especially of wheat and oat. Polypeptides that may be mentioned, for example, are the potassium salt of hydrolysed lauroyl wheat protein, sold under the name Aminofoam W OR by the company Croda, the triethanolamine salt of hydrolysed cocoyl soya bean protein, sold under the name May-Tein SY by the company Maybrook, the sodium salt of oat lauroyl amino acids, sold under the name Proteol Oat by the company SEPPIC, collagen hydrolysate grafted onto coconut fatty acid, sold under the name Geliderm 3000 by the company Deutsche Gelatine, soya bean proteins acylated with hydrogenated coconut acids, sold under the name Proteol VS 22 by the company SEPPIC.

The anionic alkyl-polyglucoside derivatives may especially be citrates, tartrates, sulphosuccinates, carbonates and glycerol ethers obtained from alkyl polyglucosides. Examples that may be mentioned are the sodium salt of cocoylpolyglucoside tartaric ester (1,4), sold under the name Eucarol AGE-ET by the company Cesalpinia, the disodium salt of cocoylpolyglucoside sulphosuccinic ester (1,4), sold under the name Essai 512 MP by the company SEPPIC, the sodium salt of cocoylpolyglucoside citric ester (1,4) sold under the name Eucarol AGE-EC® by the company Cesalpinia. Another anionic holoside derivative may be sodium dodecyl-D-galactoside uronate sold under the name Dodecyl-D-Galactoside Uronate de Sodium by the company Soliance.

Fatty acid soaps that may be used as anionic surfactants are fatty acids of natural or synthetic origin, salified with a mineral or organic base. The fatty chain may contain from 6 to 22 carbon atoms and preferably from 8 to 18 carbon atoms. The mineral or organic base may be chosen from alkali metals and alkaline-earth metals, amino acids and amino alcohols. Salts that may be used, for example, are the sodium, potassium, magnesium, triethanolamine, N-methylglucamine, lysine and arginine salts. Soaps that may be mentioned, for example, are the potassium or sodium salts of lauric, myristic, palmitic or stearic acid (potassium or sodium laurate, myristate, palmitate or stearate), and mixtures thereof.

Amphoteric and zwitterionic surfactants that may be used, for example, are betaines, N-alkylamidobetaines and derivatives thereof, glycine derivatives, sultaines, alkyl polyaminocarboxylates and alkylamphoacetates, and mixtures thereof.

Betaines that may be mentioned, for example, are cocobetaine, for instance the product sold under the name Dehyton AB-30 by the company Henkel, laurylbetaine, for instance the product sold under the name Genagen KB by the company Clariant, oxyethylenated (10 EO) laurylbetaine, for instance the product sold under the name Laurylether (10 EO) Betaine by the company Shin Nihon Rica, oxyethylenated stearylbetaine (10 EO), for instance the product sold under the name Stearylether (10 EO) Betaine by the company Shin Nihon Rica.

Examples of N-alkylamidobetaines and derivatives thereof that may be mentioned are cocoamidopropyl betaine sold under the name Lebon 2000 HG by the company Sanyo, or sold under the name Empigen BB by the company Albright & Wilson, and lauramidopropyl betaine sold under the name Rewoteric AMB12P by the company Witco.

Examples of sultaines that may be mentioned include cocoylamidopropylhydroxysulphobetaine sold under the name Crosultaine C-50 by the company Croda.

Examples of alkyl polyaminocarboxylates (APAC) that may be mentioned are sodium cocoylpolyaminocarboxylate, sold under the name Ampholak 7 CX/C and Ampholak 7 CX by the company Akzo Nobel, sodium stearylpolyamidocarboxylate, sold under the name Ampholak 7 TX/C by the company Akzo Nobel, and sodium carboxymethyloleylpolypropylamine sold under the name Ampholak X07/C by the company Akzo Nobel.

Examples of alkylamphoacetates that may be mentioned are N-disodium N-cocoyl-N-carboxymethoxy-ethyl-N-carboxymethylethylenediamine (CTFA name: disodium cocamphodiacetate), for instance the product sold under the name Miranol C2M Concentré NP by the company Rhodia Chimie, and N-sodium N-cocoyl-N-hydroxyethyl-N-carboxymethylethylenediamine (CTFA name: sodium cocamphoacetate).

The aqueous phase may optionally also comprise a gelling agent in a concentration by mass of from 0.01 to 20% of the total weight of the composition.

In the foaming compositions of the invention, the aqueous phase preferably consists of a physiologically acceptable medium allowing a topical application and especially a cosmetic application.

In the present patent application, the expression "physiologically acceptable medium" means a medium that is compatible with all keratin materials such as the skin, including the scalp, the nails, mucous membranes, the eyes and the hair or any other area of body skin.

The physiologically acceptable medium for the foaming compositions of the invention comprises water. The amount of water may range from 30 to 99.98% by weight and preferably from 40 to 95% by weight relative to the total weight of the composition.

The water used may be, besides water, a floral water such as cornflour water, a mineral water such as eau de Vittel, eau de Lucas or eau de la Roche Posay and/or a spring water.

The physiologically acceptable medium may contain, besides water, one or more solvents chosen from lower alcohols containing from 1 to 8 carbon atoms, such as ethanol; polyols such as glycerol; glycols, for instance butylene glycol, isoprene glycol, propylene glycol, polyethylene glycols such as PEG-8; sorbitol; sugars such as glucose, fructose, maltose, lactose and sucrose; and mixtures thereof. The amount of solvent(s) may range from 0.5% to 30% by weight and preferably from 5% to 20% by weight relative to the total weight of the composition.

The foaming compositions of the invention may also contain adjuvants commonly used in cosmetics and dermatology, such as mineral or organic fillers, hydrophilic or lipophilic active agents, preserving agents, gelling agents, plasticizers, antioxidants, fragrances, odour absorbers, UV screening agents, sequestering agents (EDTA), acidic or basic pH regulators or buffers, and dyestuffs (pigments or colorants or nacres). The amounts of these various additives are those conventionally used in the fields under consideration, and, for example, from 0.01% to 20% of the total weight of the composition. Needless to say, a person skilled in the art will take care to select the optional compound(s) to be added to the foaming compositions according to the invention such that the advantageous properties intrinsically associated with these compositions are not, or are not substantially, adversely affected by the envisaged addition.

The term "fillers" should be understood as meaning colourless or white, mineral or synthetic, lamellar or non-lamellar particles intended to give body or rigidity to the composition and/or softness, a matt effect and uniformity to make-up. Fillers that may especially be mentioned are talc, mica, silica, boron nitride, bismuth oxychloride, kaolin, Nylon powders such as Nylon-12 (Orgasol sold by the company Atochem), polyethylene powders, Teflon (tetrafluoroethylene polymer powders), polyurethane powders, polystyrene powders, polyester powders, optionally modified starch, copolymer microspheres, such as those sold under the name Expancel by the company Nobel Industrie, microsponges, for instance Polytrap sold by the company Dow Corning, silicone resin microbeads such as those sold by the company Toshiba under the name Tospearl, precipitated calcium carbonate, magnesium carbonate, magnesium hydrocarbonate, hydroxyapatite, hollow silica microspheres (Silica Beads from the company Maprecos), glass or ceramic microcapsules, metal soaps derived from organic carboxylic acids containing from 8 to 22 carbon atoms and preferably from 12 to 18 carbon atoms, for example zinc, magnesium or lithium stearate, zinc laurate or magnesium myristate, and mixtures thereof.

The term "pigments" should be understood as meaning white or coloured, mineral or organic particles, insoluble in the medium, that are intended to colour and/or opacify the composition. They may be white or coloured, mineral and/or organic, and of standard or nanometric size. Among the mineral pigments and nanopigments that may be mentioned are titanium dioxide, zirconium dioxide or cerium dioxide, and also zinc oxide, iron oxide or chromium oxide, nanotitaniums (titanium dioxide nanopigments), nanozincs (zinc oxide nanopigments) and ferric blue. Among the organic pigments that may be mentioned are carbon black and lakes, for instance calcium, barium, aluminium or zirconium salts, of acidic dyes such as halo acid dyes, azo dyes or anthraquinone dyes.

The term "nacres" should be understood as meaning iridescent particles that reflect light. Among the nacres that may be envisaged, mention may be made of natural mother-of-pearl, mica coated with titanium oxide, with iron oxide, with natural pigment or with bismuth oxychloride, and also coloured titanium mica.

A gelling agent may be added to the compositions of the invention in order to adjust the texture of the composition and to gain access to a wide range of textures from a milk to a cream. As already mentioned above, the compositions according to the invention can at low temperature, for example at room temperature, "in the jar", provide any desirable texture. There is no restriction as regards the texture that the composition can have, before application. In particular, the composition does not necessarily need to contain a gelling agent in order to obtain a gelled foam when applied. Specifically, by virtue of the specific polymer included in the composition of the invention, the foam obtained during the increase in temperature taking place, for example, when the composition is applied, especially to the skin, is gelled and stable, irrespective of the texture or the form of the foaming composition in the jar before application. Thus, a gelling agent will be included in the composition only if it is desired for the said composition to have a gelled appearance, this appearance being, according to the invention, only one particular appearance among the multitude of appearances, textures and forms that the foaming composition may have.

However, according to one preferred embodiment of the invention, the composition contains little or no gelling agent (less than 0.1%).

The gelling agents that may be used may be hydrophilic gelling agents. Examples of hydrophilic gelling agents that may be mentioned in particular are carboxyvinyl polymers (carbomer), acrylic copolymers such as acrylate/alkylacrylate copolymers, poly-acrylamides, polysaccharides, natural gums and clays.

The composition may optionally contain an oily phase.

The oily phase preferably comprises at least one oil.

As oils which can be used in the composition of the invention, mention may be made for example of:

hydrocarbon-based oils of animal origin, such as perhydrosqualene;

hydrocarbon-based oils of plant origin, such as liquid triglycerides of fatty acids containing from 4 to 10 carbon atoms, such as heptanoic or octanoic acid triglycerides or alternatively, for example, sunflower oil, corn oil, soybean oil, marrow oil, grapeseed oil, sesame oil, hazelnut oil, apricot oil, macadamia oil, arara oil, castor oil, avocado oil, caprylic/capric acid triglycerides such as those sold by the company Stearineries Dubois or those sold under the names Miglyol 810, 812 and 818 by the company Dynamit Nobel, jojoba oil or karite butter;

synthetic esters and ethers, in particular of fatty acids, such as the oils of formulae $R^1COOR^2$ and $R^1OR^2$ in which $R^1$ represents a fatty acid residue containing from 8 to 29 carbon atoms and $R^2$ represents a branched or unbranched hydrocarbon-based chain containing from 3 to 30 carbon atoms, such as, for example, purcellin oil, isononyl isononanoate, isopropyl myristate, 2-ethylhexyl palmitate, 2-octyl-dodecyl stearate, 2-octyldodecyl erucate or isostearyl isostearate; hydroxylated esters such as isostearyl lactate, octyl hydroxystearate, octyldodecyl hydroxystearate, diisostearyl malate, triisocetyl citrate, and fatty alcohol heptanoates, octanoates and decanoates; polyol esters such as propylene glycol dioctanoate, neopentyl glycol diheptanoate and diethylene glycol diisononanoate; and pentaerythritol esters such as pentaerythrityl tetraisostearate;

linear or branched hydrocarbons of mineral or synthetic origin, such as volatile or non-volatile liquid paraffins and derivatives thereof, petroleum jelly, polydecenes or hydrogenated polyisobutene such as Parleam oil;

natural or synthetic essential oils such as, for example, eucalyptus oil, hybrid lavender oil, lavender oil, vetiver oil, Litsea cubeba oil, lemon oil, sandalwood oil, rosemary oil, camomile oil, savory oil, nutmeg oil, cinnamon oil, hyssop oil, caraway oil, orange oil, geraniol oil, cade oil and bergamot oil;

fatty alcohols containing from 8 to 26 carbon atoms, such as cetyl alcohol, stearyl alcohol, and the mixture thereof (cetylstearyl alcohol), octyldodecanol, 2-butyloctanol, 2-hexyldecanol, 2-undecylpentadecanol, oleyl alcohol or linoleyl alcohol;

partially hydrocarbon-based and/or silicone-based fluoro oils such as those described in document JP-A-2-295912;

silicone oils such as volatile or non-volatile polydimethylsiloxanes (PDMSs) containing a linear or cyclic silicone chain, which are liquid or pasty at room temperature, in particular cyclopolydimethylsiloxanes (cyclomethicones) such as cyclohexasiloxane; polydimethylsiloxanes comprising alkyl, alkoxy or phenyl groups, pendent or at the end of a silicone chain, these groups containing from 2 to 24 carbon atoms; phenylsilicones such as phenyl trimethicones, phenyl dimethicones, phenyltrimethyl-siloxydiphenylsiloxanes, diphenyl dimethicones, diphenylmethyldiphenyltrisiloxanes, 2-phenylethyl trimethylsiloxysilicates and polymethylphenylsiloxanes;

mixtures thereof.

The term "hydrocarbon-based oil" in the list of the abovementioned oils embraces any oil comprising predominantly carbon and hydrogen atoms, and optionally ester, ether, fluoro, carboxylic acid and/or alcohol groups.

The other fatty substances which may be present in the oily phase are, for example, fatty acids containing from 8 to 30 carbon atoms, for instance stearic acid, lauric acid, palmitic acid and oleic acid; waxes, for example lanolin, beeswax, carnauba wax, candelilla wax, paraffin wax, lignite wax or microcrystalline waxes, ceresine or ozokerite, synthetic waxes, for instance polyethylene waxes and Fischer-Tropsch waxes; gums such as silicone gums (dimethiconol); silicone resins such as trifluoromethyl-C1-4-alkyldimethicone and trifluoro-propyldimethicone; and silicone elastomers, for instance the products sold under the names "KSG" by the company Shin-Etsu, under the names "Trefil", "BY29" or "EPSX" by the company Dow Corning or under the names "Gransil" by the company Grant Industries.

These fatty substances may be chosen in a varied manner by a person skilled in the art in order to prepare a composition having the desired properties, for example consistency or texture properties.

When it is present, the amount of oily phase may range, for example, from 0.01% to 50% by weight and preferably from 0.1% to 30% by weight relative to the total weight of the composition.

The foaming compositions of the invention may especially be in the form of a cosmetic composition, especially a cleansing or make-up-removing composition, which may be applied to the skin, including the scalp, the nails, the hair, the eyelashes, the eyebrows, the eyes, mucous membranes and semi-mucous membranes, and any other area of body or facial skin.

The composition according to the invention may constitute a shower gel, a facial cleansing product, a make-up-removing product, a shampoo, a shaving foam or gel, etc.

Starting with the foaming composition according to the invention, that is to say a composition capable of foaming, but which does not foam especially in the container containing it, during storage, a foam is obtained, that is to say a dispersion of bubbles of gas in an aqueous continuous phase, by exerting a mechanical action, such as an agitation, on the said composition. This mechanical action may be due to the action of the user's fingers during the application or it may be due to the passage of the composition through a nozzle or other static mixer allowing, for example, a stream of the composition to be mixed with a stream of gas to form bubbles of this gas in the aqueous phase. The gas included in the foam is generally air, but it may also be nitrogen or other propellant gases known in such applications, in particular hydrocarbon-based gases such as, for example, propane, n-butane or isobutane, and mixtures thereof.

A subject of the invention is also the cosmetic use of the foaming composition as defined above for cleansing and/or removing make-up from the skin, the scalp, the nails, the eyelashes, the eyebrows, the eyes, mucous membranes, semi-mucous membranes and/or the hair.

The foaming compositions according to the invention may, for example, be used in two ways:
- the first use consists in spreading the gel in the hands, applying it to the face or the body and then massaging it in the presence of water to develop the foam directly on the face or the body,
- the other possible use of this type of product consists in developing the foam in the palms of the hands before applying it to the face or the body.

The foam is then rinsed off.

Another subject of the invention consists of a cosmetic process for cleansing and/or removing make-up from keratin materials (skin, scalp, nails, eyelashes, eyebrows, eyes, mucous membranes, semi-mucous membranes and/or hair), characterized in that the composition of the invention is applied to the keratin materials in the presence of water, and the foam formed and the soiling residues are removed by rinsing with water.

Other characteristics and advantages of the invention will emerge more clearly on reading the description which follows, given by way of non-limiting illustration, with reference to the attached drawings in which:

FIG. 1 is a graph which shows the viscosity V (in Pa.s) as a function of the temperature T (° C.) of an aqueous solution of polymer 2 of Table 1, at 1% by weight (Example 2);

FIG. 2 is a graph which shows the viscosity V (in Pa.s) as a function of the temperature T (° C.) of an aqueous solution containing polymer 2 of Table 1 at 1% by weight and a surfactant (Example 3).

DETAILED DESCRIPTION OF THE EMBODIMENTS

The examples which follow illustrate the preparation of foaming compositions according to the invention comprising polymers comprising specific water-soluble units and units with an LCST.

The polymers used in these examples consist of a polyacrylic acid (PAA) backbone bearing side chains or grafts consisting of specific units with an LCST. They are characterized by the molar mass of the water-soluble backbone (polyacrylic acid), the chemical nature of the chains with an LCST, their proportion by mass in the polymer and their molar mass.

The characteristics of the polymers used are given in Table 1.

TABLE 1

| | Water-soluble backbone | Grafts (units with an LCST) | Proportion: units with an LCST in the final polymer (by weight) | Degree of grafting (mol %) |
|---|---|---|---|---|
| Polymer 1 | Polyacrylic acid; MW = 450 000 | $(EO)_6(PO)_{39}$ random Jeffamine M-2005; MW = 2600 | 51% | 3.9% |
| Polymer 2 | Polyacrylic acid; MW = 550 000 | Poly-N-isopropyl-acrylamide (pNIPAM) MW = 10 000 | 49% | 0.9% |

These polymers are prepared in the following manner.

Preparation of Polymer 1

3 g of polyacrylic acid with an average molar mass of 450 000 g/mol (Aldrich) are dissolved in 220 ml of N-methylpyrrolidone in a 500 ml reactor equipped with a condenser, with stirring at 60° C. for 12 hours.

4.181 g of monoamino random $(EO)_6(PO)_{39}$ copolymer with a molar mass of 2600 g/mol having a cloud point, at a concentration of 1% by weight in water, of 16° C. (Jeffamine M-2005 from Huntsman) are dissolved in 50 ml of N-methylpyrrolidone with stirring, at 20° C., for 15 minutes. The solution obtained is added dropwise to the reaction medium containing the polyacrylic acid, with vigorous stirring at 60° C.

2.158 g of dicyclohexylcarbodiimide are dissolved in 30 ml of N-methylpyrrolidone with stirring at 20° C. for 15 minutes. The solution obtained is added dropwise to the reaction medium containing the polyacrylic acid and the monoamino random $(EO)_6(PO)_{39}$ copolymer, with vigorous stirring at 60° C. The final mixture is stirred for 12 hours at 60° C.

The mixture is cooled to 20° C. and is then placed in a refrigerator at 4° C. for 24 hours. The crystals of dicyclohexylurea formed are removed by filtration of the reaction medium.

The polymer is then neutralized with 19 g of 35% sodium hydroxide (4-fold excess relative to the number of moles of acrylic acid), leading to its precipitation. After standing for 12 hours, the reaction medium is filtered so as to recover the precipitated polymer. This polymer is dried under vacuum at 35° C. for 24 hours.

13.55 g of solid are recovered and are dissolved in 2 l of deionized water. This solution is ultrafiltered using a Millipore ultrafiltration system containing a membrane with the cutoff threshold set at 10 000 daltons. The solution thus purified is freeze-dried so as to collect the polymer in solid form.

7.05 g of polyacrylic acid (450 000 g/mol) grafted with 3.9% (on a molar basis) of monoamino random $(EO)_6(PO)_{39}$ copolymer are obtained.

The proportion by mass of the units with an LCST in the final polymer is 51%.

The polymer thus obtained has a solubility in water, at 20° C., of at least 10 g/l.

Preparation of Polymer 2

Polymer 2, which comprises poly-N-isopropylacrylamide (pNIPAM) grafts, is prepared by a 2-step process:

1) Synthesis of pNIPAM Oligomers Bearing a Reactive Amino End 8 g of N-isopropylacrylamide and 80 ml of dimethyl sulphoxide are introduced into a 250 ml three-necked round-bottomed flask equipped with a condenser and a nitrogen inlet. This mixture is heated with stirring at 29° C. using a water bath and placed under a nitrogen. After 45 minutes, 0.161 g of aminoethanethiol hydrochloride predissolved in 4 ml of dimethyl sulphoxide is added to the reaction medium. 5 minutes later, 0.191 g of potassium persulphate dissolved in 8 ml of dimethyl sulphoxide is added to the reaction medium. This reaction medium is stirred under a nitrogen atmosphere for 3 hours at 29° C.

The poly-N-isopropylacrylamide (pNIPAM) oligomers synthesized are isolated by precipitation from the reaction medium in a mixture of acetone (40% by volume) and hexane (60%).

2) Grafting of the pNIPAM Oligomers Onto Polyacrylic Acid 3 g of polyacrylic acid with a molar mass of 550 000 g/mol are dissolved in 100 ml of 1-methyl-2-pyrrolidone in a 250 ml three-necked round-bottomed flask equipped with a condenser, with stirring at 60° C. for 12 hours. 3.757 g of pNIPAM oligomers predissolved in 25 ml of 1-methyl-2-pyrrolidone are introduced dropwise into the reaction medium with stirring. 15 minutes later, 0.776 g of dicyclohexylcarbodiimide predissolved in 25 ml of 1-methyl-2-pyrrolidone is introduced dropwise into the reaction medium with vigorous stirring. The reaction medium is maintained at 60° C. for 12 hours with stirring.

The reaction medium is then cooled to 20° C. and then placed in a refrigerator at 4° C. for 24 hours. The dicyclohexylurea crystals formed are then removed by filtration. The polymer is then neutralized using 19 g of 35% sodium hydroxide (4-fold excess relative to the number of moles of acrylic acid), leading to its precipitation. After standing for 12 hours, the reaction medium is filtered so as to recover the precipitated polymer. This polymer is dried under vacuum at 35° C. for 24 hours.

10.2 g of solid are recovered and are dissolved in 2 liters of deionized water. This solution is ultrafiltered using a Millipore ultrafiltration system containing a membrane with the cutoff threshold set at 10 000 daltons. The solution thus purified is freeze-dried so as to collect the polymer in solid form.

4.8 g of polyacrylic acid (450 000 g/mol) grafted with 0.9% (on a molar basis) of poly-N-isopropylacrylamide are obtained.

The proportion by mass of the units with an LCST in the final polymer is 49%.

The critical aggregation concentrations (CAC) of the two polymers prepared above are determined by rheology, according to the method described above, using a Haake RS 150 rheometer equipped with a cone/plate geometry (35 mm, 2°) and a thermostatic bath, so as to maintain the temperature between 5 and 80° C. The measurements were carried out in the flow mode at a shear rate of 10 $s^{-1}$, by varying the temperature from 15 to 50° C. at a rate of 0.5° C./minute.

For polymer 1 in 0.2 M NaCl; the critical aggregation concentration (CAC) is about 1% by weight, whereas for polymer 2 in pure water, the critical aggregation concentration is about 0.3% by weight.

EXAMPLE 1

This example relates to surfactant-free foaming formulations containing polymer 1.

The stabilities at 15 and 50° C. of the foams obtained from these formulations and also their viscosity at these temperatures are studied.

Preparation of the Foaming Formulation

The foaming formulation 1 below is prepared by simple dissolution with stirring of the appropriate amount of polymer in powder form in a 0.2 M solution of NaCl in water, at room temperature, to give the desired concentration by mass of the polymer, i.e. 3% by weight.

Formulation 1

Polymer 1 in water at 3% (by weight), 0.2 M NaCl.

Process for Obtaining the Foam

The foams were obtained from the aqueous polymer solution prepared above (5 g of solution in 10 ml pill bottles) subjected to stirring using a Diax 600 machine (Heidolph) for 5 minutes at 8000 rpm and then for 1 minute at 13 500 rpm. The shaft used has an outside diameter of 10 mm (reference 10F).

Stability of the Foam Obtained

The change in the macroscopic appearance of the foams thus obtained was monitored over time at t=0, 1 hour and 2 hours 30 minutes; the foaming power is proportionately greater the greater the foam height.

At 15° C., the foam initially occupies 100% of the volume. After 1 hour, 50% of the volume is in the form of foam. After 2 hours 30 minutes, there is no longer any foam.

At 50° C., the foam initially occupies 100% of the volume. After 1 hour, 95% of foam remains. After 2 hours 30 minutes, 90% of the volume is still a foam.

Polymer 1 makes it possible, in aqueous solution at a low concentration (Cp=3%, NaCl=0.2 M) to obtain a foaming system, from 15 to 50° C., without surfactant. The stability of the foam obtained is greater at 50 than at 15° C., this behaviour possibly being correlated to the heat-induced gelling properties of polymer 1.

Measurement of the Viscosity

The rheological measurements were performed using a Haake RS150 rheometer equipped with a cone/plate geometry (35 mm, 2°) and a thermostatic bath so as to maintain the temperature between 5 and 80° C. The measurements were carried out in the flow mode, at an imposed shear rate equal to 10 s$^{-1}$, by varying the temperature from 15 to 50° C. at a rate of 0.5° C./min.

The solution of polymer 1 at 3% (by weight), 0.2 mol/l NaCl, has the following characteristics:

viscosity at 15° C. (ls$^{-1}$)=0.01 Pa.s;

viscosity at 50° C. (ls$^{-1}$)=0.5 Pa.s.

The gelling power of polymer 1, above 25° C., makes it possible to obtain a gelled foam that is easier to apply to the skin than a fluid formulation.

EXAMPLE 2

This example relates to surfactant-free foaming formulations containing polymer 2. The stabilities at 15 and 38° C. of the foams obtained from these formulations, and also their viscosity at these temperatures, are studied.

Preparation of the Foaming Formulation

Foaming formulation 2 is prepared in the same way as in Example 1, but pure water is used and the polymer concentration is 1% by weight.

Formulation 2

Polymer 2 in water at 1% (by weight).

Process for Obtaining the Foam

The foams were obtained from the aqueous polymer solution prepared above (5 g of solution in 10 ml pill bottles) subjected to stirring using a Diax 600 machine (Heidolph) for 5 minutes at 8000 rpm and then for 1 minute at 13 500 rpm. The shaft used has an outside diameter of 10 mm (reference 10F).

Stability of the Foam Obtained

The change in the macroscopic appearance of the foams thus obtained was monitored over time at t=30 hours and 27 days for T=15° C. and at t=51 hours and 27 days for T=38° C.; the foaming power is proportionately greater the greater the foam height.

At 15° C., the whole composition is in the form of foam. After 30 hours, 50% is a foam and after 27 days, there is no longer any foam.

At 38° C., 100% of the composition is a foam. After 51 hours, there is still 100% foam. After 27 days, 50% foam remains.

Polymer 2 makes it possible, in aqueous solution at a low concentration (Cp=1%), to obtain a foaming system, from 15 to 38° C., without surfactant. The stability of the foam obtained is better at 38 than at 15° C., this behaviour possibly being correlated with the heat-induced gelling properties of Polymer 2.

Measurement of the Viscosity

The rheological measurements were performed using a Haake RS150 rheometer equipped with a cone/plate geometry (35 mm, 2°) and a thermostatic bath so as to maintain the temperature between 5 and 80° C. The measurements were carried out in the flow mode, at an imposed shear rate equal to 10 s$^{-1}$, by varying the temperature from 20 to 40° C. at a rate of 0.5° C./min.

The figure below (FIG. 1) shows the change in viscosity from 20 to 40° C. of an aqueous solution of Polymer 2 at 1% (by weight).

Effect of heat-induced gelling above 27° C.:

at 25° C.: 0.15 Pa.s.

at 38° C.: 0.78 Pa.s.

The gelling power of Polymer 2, above 27° C., makes it possible to obtain a gelled foam which is easier to apply to the skin than a fluid formulation.

EXAMPLE 3

This example relates to foaming formulations containing 3% of an alkyl polyglucoside surfactant and 1% of polymer 2.

The stabilities at 15 and 38° C. of the foams obtained from these formulations, and also their viscosity at these temperatures, are studied.

The surfactant used is a $C_{10-14}$ alkyl polyglucoside sold under the name Oramix NS10 by SEPPIC.

Preparation of the foaming formulation: the following foaming formulations are prepared in the same way as in Example 1.

Formulation 3A

Surfactant at 3% (by weight)+polymer 2 at 1% in aqueous solution.

Formulation 3B

Surfactant at 3% (by weight) in aqueous solution.

Process for Obtaining the Foam

The foams were obtained from aqueous solutions of surfactant in the presence or absence of the polymers, prepared above (5 g of solution in 10 ml pill bottles) subjected to stirring using a Diax 600 machine (Heidolph) for 5 minutes at 8000 rpm and then for 1 minute at 13 500 rpm. The shaft used has an outside diameter of 10 mm (reference 10F).

Stability of the Foams Obtained

The change in the macroscopic appearance of the foams thus obtained was monitored over time at t=0 and t=7 hours at 15 and 38° C.; the foaming power is proportionately greater the greater the foam height.

At 15° C., 100% of compositions 3A and 3B are in the form of foam. After 7 hours, 70% foam remains in both cases.

At 38° C., 100% of compositions 3A and 3B are in the form of foam. After 7 hours, 100% foam remains for formulation 3A and only 50% for formulation 3B.

The introduction of Polymer 2 at a low concentration (Cp=1%) into a foaming formulation containing 3% of alkyl polyglucoside surfactant makes it possible to improve the stability of the foam beyond the gel point of Polymer 2 (27° C. for a concentration in water equal to 1%). The stability of the foam is greater at 38 than at 15° C., this behaviour possibly being correlated with the heat-induced gelling properties of Polymer 2.

Measurements of the Viscosity

The rheological measurements were performed using a Haake RS150 rheometer equipped with a cone/plate geometry (35 mm, 2°) and a thermostatic bath so as to maintain the temperature between 5 and 80° C. The measurements were carried out in the flow mode, at an imposed shear rate equal to 10 s$^{-1}$, by varying the temperature from 20 to 40° C. at a rate of 0.5° C./min.

The figure below (FIG. 2) shows the change in viscosity from 20 to 45° C. of an aqueous solution containing the surfactant (3% by weight) and Polymer 2 (1% by weight).

Heat-induced gelling effect at and above 25° C.:

at 20° C.: 0.13 Pa.s.

at 38° C.: 0.63 Pa.s.

EXAMPLE 4

In this example, a fluid foaming cosmetic composition, which gels when applied, is prepared.

This composition is as follows (% by weight).

| | |
|---|---|
| Glycerol | 5% |
| Polymer 1 | 3% |
| $C_{10-14}$ polyglucoside (Oramix NS 10 from SEPPIC) | 5% |
| Preserving agent | 0.4% |
| Sodium ethylenediaminetetraacetate | 0.2% |
| Demineralized water | 86.4% |

Preparation Method

This foaming composition is obtained by dissolving polymer 1 in powder form in demineralized water with stirring at room temperature for 3 hours; the other constituents are then introduced into this solution and stirring is continued for 30 minutes.

The formulation obtained is a foaming composition that is fluid at room temperature and that gels when applied to the skin; this change in texture is pleasant and facilitates the application.

REFERENCES

[1] D. Hourdet et al., Polymer, 1994, Vol. 35, No. 12, pages 2624–2630.
[2] F. L'Alloret et al., Coll. Polym. Sci., 1995, Vol. 273, No. 12, pages 1163–1173.
[3] F. L'Alloret, Revue de l'Institut Francais du Pétrole [Review of the French Petroleum Institute], 1997, Vol. 52, No. 2, pages 117–128.
[4] EP-A-0 583 814.
[5] EP-A-0 629 649.
[6] EP-A-95 24430.
[7] U.S. Pat. No. 5,939,485.
[8] WO-A-97 00275.
[9] WO-A-98 48768.
[10] WO-A-00 35961.
[11] Articles by Taylor et al., Journal of Polymer Science, part A: Polymer Chemistry, 1975, 13, 2551.
[12] J. Bailey et al., Journal of Applied Polymer Science, 1959, 1, 56.
[13] Heskins et al., Journal of Macromolecular Science, Chemistry A2, 1968, 1441.
[14] EP-A-0 566 438.
[15] FR-A-2 739 556.

What is claimed is:

1. A heat-induced gelling foaming composition comprising an aqueous phase, said aqueous phase comprising a physiologically acceptable medium suitable for topical application; and a polymer comprising water-soluble units and units having in water a lower critical solution temperature LCST, the heat-induced demixing temperature in aqueous solution of said units with an LCST being from 5 to 40° C. for a concentration of said units in water of 1% by mass, and the concentration of said polymer in said composition being such that its gel point is in the range from 5 to 40° C.

2. The composition according to claim 1, in which the heat-induced demixing temperature in aqueous solution of the units with an LCST of the polymer is from 10 to 35° C. for a concentration by mass in water of 1% of the said units.

3. The composition according to claim 2, in which the concentration of the polymer in the composition is such that its gel point is in the range from 10 to 35° C.

4. The composition according to claim 1, in which the polymer is in the form of a block polymer comprising blocks consisting of water-soluble units alternating with blocks of units with an LCST, or in the form of a grafted polymer whose backbone is formed by water-soluble units, said backbone bearing grafts of units with an LCST.

5. The composition according to claim 1, in which the water-soluble units are totally or partially capable of being obtained by polymerization, by polycondensation, or comprise totally or partially of natural polymers or modified natural polymers.

6. The composition according to claim 5, in which the water-soluble units axe totally or partially capable of being obtained by polymerization, of at least one monomer selected from the group consisting of:

(meth)acrylic acid;

vinyl monomers of formula (I) below:

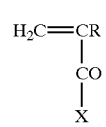

in which:

R is H, —$CH_3$, —$C_2H_5$ or —$C_3H_7$, and

X is:

alkyl oxides of —OR' type in which R' is a linear or branched, saturated or unsaturated hydrocarbon-based radical containing from 1 to 6 carbon atoms, optionally substituted with at least one halogen atom selected from the group consisting of iodine, bromine, chlorine and fluorine; a sulphonic (—$SO_3^-$), sulphate (—$SO_4^-$), phosphate (—$PO_4H_2$); hydroxyl (—OH); primary amine (—$NH_2$); secondary amine (—$NHR_1$), tertiary amine (—$NR_1R_2$) or quaternary amine (—$N^+R_1R_2R_3$) group with $R_1$, $R_2$ and $R_3$ being, independently of each other, a linear or branched, saturated or unsaturated hydrocarbon-based radical containing 1 to 6 carbon atoms, with the proviso that the sum of the carbon atoms of $R'+R_1R_2+R_3$ does not exceed 7; and —$NH_2$, —$NHR_4$ and —$NR_4R_5$ groups in which $R_4$ and $R_5$ are, independently of each other, linear or branched, saturated or unsaturated hydrocarbon-based radicals containing 1 to 6 carbon atoms, with the proviso that the total number of carbon atoms of $R_4+R_5$ does not exceed 7, the said $R_4$ and $R_5$ optionally being substituted with a halogen atom selected from the group consisting of iodine, bromine, chlorine and fluorine); a hydroxyl (—OH); sulphonic (—$SO_3^-$); sulphate (—$SO_4^-$); phosphate (—$PO_4H_2$); primary amine (—$NH_2$); secondary amine (—$NHR_1$), tertiary amine (—$NR_1R_2$) and/or quaternary amine (—$N^+R_1R_2R_3$) group with $R_1$, $R_2$ and $R_3$ being, independently of each other, a linear or branched, saturated or unsaturated hydrocarbon radical containing 1 to 6 carbon atoms, with the proviso that the sum of the carbon atoms of $R_4+R_5+R_1+R_2+R_3$ does not exceed 7;

maleic anhydride;

itaconic acid;

vinyl alcohol of formula $CH_2$=CHOH;

vinyl acetate of formula $CH_2$=CH—$OCOCH_3$;

N-vinyllactams such as N-vinylpyrrolidone, N-vinylcaprolactam and N-butyrolactam;

vinyl ethers of formula $CH_2$=$CHOR_6$ in which $R_6$ is a linear or branched, saturated or unsaturated hydrocarbon radical containing from 1 to 6 carbon atoms;

water-soluble styrene derivatives, especially styrene sulphonate;

dimethyldiallylammonium chloride; and vinylacetamide.

7. The composition according to claim 5, in which the water-soluble units of the polymer comprises totally or partially of polycondensates or of natural polymers or modified natural polymers of one or more polymers selected from the group consisting of:

water-soluble polyurethanes;

xanthan gum;

alginates and derivatives thereof;

cellulose derivatives;

galactomannans and derivatives thereof; and polyethyleneimine.

8. The composition according to claim 5, in which the water-soluble units of the polymer have a molar mass ranging from 1000 g/mol to 5 000 000 g/mol when they constitute the water-soluble backbone of a grafted polymer, or a molar mass ranging from 500 g/mol to 100 000 g/mol when they constitute a block of a multiblock polymer.

9. The composition according to claim 1, in which the units with an LCST of the polymer comprises of one or more polymers selected from the group consisting of:

polyethers;

polyvinyl methyl ethers;

polymeric and copolymeric N-substituted acrylamide derivatives with an LCST; and polyvinylcaprolactam and vinylcaprolactam copolymers.

10. The composition according to claim 1, in which the units with an LCST of the polymer comprises polypropylene oxide (PPO)$_n$ with n being an integer from 10 to 50, or of random copolymers of ethylene oxide (EO) and of propylene oxide (PO), represented by the formula:

$$(EO)_m(PO)_n$$

in which m is an integer of 1 to 40, and n is an integer ranging of 10 to 60.

11. The composition according to claim 10, in which the molar mass of the units with an LCST of the polymer is from 500 to 5300 g/mol.

12. The composition according to claim 1, in which the units with an LCST of the polymer comprise a polymer selected from the group consisting of poly-N-isopropylacrylamide, poly-N-ethylacrylamide, and copolymers of N-isopropylacrylamide or of N-ethylacrylamide and of a vinyl monomer selected from the group consisting of monomers having formula (I):

$$\underset{\underset{\underset{X}{|}}{\underset{CO}{|}}}{H_2C=CR} \quad (I)$$

in which:

R is H, —CH$_3$, —C$_2$H$_5$ or —C$_3$H$_7$, and

X is:

alkyl oxides of —OR' type in which R' is a linear or branched, saturated or unsaturated hydrocarbon-based radical containing from 1 to 6 carbon atoms, optionally substituted with at least one halogen atom selected from the group consisting of iodine, bromine, chlorine and fluorine; a sulphonic (—SO$_3^-$), sulphate (—SO$_4^-$), phosphate (—PO$_4$H$_2$); hydroxyl (—OH); primary amine (—NH$_2$); secondary amine (—NHR$_1$), tertiary amine (—NR$_1$R$_2$) or quaternary amine (—N$^+$R$_1$R$_2$R$_3$) group with R$_1$, R$_2$ and R$_3$ being, independently of each other, a linear or branched, saturated or unsaturated hydrocarbon-based radical containing 1 to 6 carbon atoms, with the proviso that the sum of the carbon atoms of R'+R$_1$+R$_2$+R$_3$ does not exceed 7; and —NH$_2$, —NHR$_4$ and —NR$_4$R$_5$ groups in which R$_4$ and R$_5$ are, independently of each other, linear or branched, saturated or unsaturated hydrocarbon-based radicals containing 1 to 6 carbon atoms, with the proviso that the total number of carbon atoms of R$_4$+R$_5$ does not exceed 7, the said R$_4$ and R$_5$ optionally being substituted with a halogen atom selected from the group consisting of iodine, bromine, chlorine and fluorine); a hydroxyl (—OH); sulphonic (—SO$_3^-$); sulphate (SO$_4^-$); phosphate (—PO$_4$H$_2$); primary amine (—NH$_2$); secondary amine (—NHR$_1$), tertiary amine (—NR$_1$R$_2$) and/or quaternary amine (—N$^+$R$_1$R$_2$R$_3$) group with R$_1$, R$_2$ and R$_3$ being, independently of each other, a linear or branched, saturated or unsaturated hydrocarbon radical containing 1 to 6 carbon atoms, with the proviso that the sum of the carbon atoms of R$_4$+R$_5$+R$_1$+R$_2$+R$_3$ does not exceed 7, maleic anhydride, itaconic acid, vinylpyrrolidone, styrene, styrene derivatives, dimethyldiallylammonium chloride, vinylacetamide, vinyl alcohol/vinyl acetate, vinyl ethers and vinyl acetate derivatives.

13. The composition according to claim 12, in which the molar mass of the units with an LCST of the polymer is from 1000 g/mol to 500 000 g/mol.

14. The composition according to claim 1, in which the units with an LCST of the polymer comprises a polyvinylcaprolactam or a copolymer of vinylcaprolactam and of a vinyl monomer selected from the group consisting of monomers corresponding to formula (I):

$$\underset{\underset{\underset{X}{|}}{\underset{CO}{|}}}{H_2C=CR} \quad (I)$$

in which:

R is H, —CH$_3$, —C$_2$H$_5$ or —C$_3$H$_7$, and

X is:

alkyl oxides of —OR' type in which R' is a linear or branched, saturated or unsaturated hydrocarbon-based radical containing from 1 to 6 carbon atoms, optionally substituted with at least one halogen atom selected from the group consisting of iodine, bromine, chlorine and fluorine; a sulphonic (—SO$_3^-$), sulphate (—SO$_4^-$), phosphate (—PO$_4$H$_2$); hydroxyl (—OH); primary amine (—NH$_2$); secondary amine (—NHR$_1$), tertiary amine (—NR$_1$R$_2$) or quaternary amine (—N$^+$R$_1$R$_2$R$_3$) group with R$_1$, R$_2$ and R$_3$ being, independently of each other, a linear or branched, saturated or unsaturated hydrocarbon-based radical containing 1 to 6 carbon atoms, with the proviso that the sum of the carbon atoms of R'+R$_1$+R$_2$+R$_3$ does not exceed 7; and —NH$_2$, —NHR$_4$ and —NR$_4$R$_5$ groups in which R$_4$ and R$_5$ are, independently of each other, linear or branched, saturated or unsaturated hydrocarbon-based radicals containing 1 to 6 carbon atoms, with the proviso that the total number of carbon atoms of $R_4+R_5$ does not exceed 7, the said $R_4$ and $R_5$ optionally being substituted with a halogen atom selected from the group consisting of iodine, bromine, chlorine and fluorine; a hydroxyl (—OH); sulphonic (—$SO_3^-$); sulphate (—$SO_4^-$); phosphate (—$PO_4H_2$); primary amine (—$NH_2$); secondary amine (—$NHR_1$), tertiary amine (—$NR_1R_2$) and/or quaternary amine (—$N^+R_1R_2R_3$) group with $R_1$, $R_2$ and $R_3$ being, independently of each other, a linear or branched, saturated or unsaturated hydrocarbon radical containing 1 to 6 carbon atoms, with the proviso that the sum of the carbon atoms of $R_4+R_5+R_1+R_2+R_3$ does not exceed 7, maleic anhydride, itaconic acid, vinylpyrrolidone, styrene and its derivatives, dimethyldiallylammonium chloride, vinylacetamide, vinyl alcohol, vinyl acetate, vinyl ethers and vinyl acetate derivatives.

15. The composition according to claim 14, in which the molar mass of the units with an LCST is from 1000 to 500 000 g/mol.

16. The composition according to claim 1, in which the proportion by mass of units with an LCST of the polymer is from 5 to 70% relative to the polymer.

17. The composition according to claim 1, in which the concentration by mass of polymer in the aqueous phase is from 0.1 to 20%.

18. The composition according to claim 1, in which the aqueous phase further comprises a foaming surfactant.

19. The composition according to claim 18, in which said foaming surfactant is nonionic.

20. The composition according to claim 1, in which the aqueous phase comprises a physiologically acceptable medium suitable for cosmetic application.

21. The composition according to claim 20, wherein the composition is a shower gel, a facial cleansing product, a make-up-removing product, a shampoo, shaving foam or a shaving gel.

22. A foam obtained by foaming the composition according to claim 1, wherein a dispersion of gas bubbles is formed in the continuous aqueous phase.

23. A method of stabilizing a foam formed from a composition comprising an aqueous phase, the method comprising adding a polymer to the aqueous phase wherein the polymer comprises water-soluble units and units having in water a lower critical solution temperature LCST, the heat-induced demixing temperature in aqueous solution of said units with an LCST being from 5 to 40° C. for a concentration of said units in water of 1% by mass, and the concentration of said polymer in said composition being such that its gel point is in the range from 5 to 40° C. of the composition.

24. A process for cleansing and/or removing make-up from keratinous materials comprising applying to the keratinous materials the composition according to claim 1, in the presence of water, forming a foam, and removing the foam formed and the soiling residues by rinsing with water.

25. The composition according to claim 4, wherein the polymer is in the form of a grafted polymer whose backbone is formed by water-soluble units, wherein said backbone bearing grafts of units with an LCST is partially crosslinked.

26. The composition according to claim 7, wherein the water-soluble units of the polymer comprises alginate derivatives and the alginate derivative is propylene glycol alginate.

27. The composition according to claim 7, wherein the water-soluble units of the polymer comprises at least one cellulose derivative and the cellulose derivative is selected from the group consisting of carboxymethylcellulose, hydroxypropylcellulose, hydroxyethylcellulose and quaternized hydroxyethylcellulose.

28. The composition according to claim 7, wherein the water-soluble units of the polymer comprise at least one galactomannan derivative and the galactomannan derivative is selected from the group consisting of Konjac gum, guar gum, hydroxypropylguar, hydroxypropylguar modified with sodium methylcarboxylate groups, and hydroxypropyltrimethylammonium guar chloride.

29. The composition according to claim 9, where the one or more polymers is a polyether and the polyether is selected from the group consisting of polyethylene oxide; polypropylene oxide; and a random copolymer of ethylene oxide and of propylene oxide.

30. The composition according to claim 10, wherein the units with an LCST comprise a random copolymer of ethylene oxide and propylene oxide represented by $(EO)_m(PO)_n$, wherein m is an integer of 2 to 20.

31. The composition according to claim 10, wherein the units with an LCST comprise a random copolymer of ethylene oxide and propylene oxide represented by $(EO)_m(PO)_n$, wherein n is an integer of 20 to 50.

32. The composition according to claim 11, wherein the molar mass of the units with an LCST of the polymer is from 1,500 to 4000 g/mol.

33. The composition according to claim 13, wherein the molar mass of the units with an LCST of the polymer is from 2000 to 50 000 g/mol.

34. The composition according to claim 15, wherein the molar mass of the units with an LCST is from 2000 to 50,000 g/mol.

35. The composition according to claim 16, wherein the proportion by mass of units with an LCST of the polymer is from 20 to 65% relative to the polymer.

36. The composition according to claim 16, wherein the proportion by mass of units with an LCST of the polymer is from 30 to 60% relative to the polymer.

37. The composition according to claim 20, in which the topical application is a cosmetic application.

38. The composition according to claim 6, in which the water-soluble units are totally or partially capable of being obtained by free-radical polymerization.

* * * * *

UNITED STATES PATENT AND TRADEMARK OFFICE
CERTIFICATE OF CORRECTION

PATENT NO. : 6,878,754 B2
DATED : April 12, 2005
INVENTOR(S) : Florence L'Alloret It is certified that error appears in the above-identified patent and that said Letters Patent is hereby corrected as shown below:

Column 24,
Line 11, "axe" should read -- are --.

Signed and Sealed this

Thirtieth Day of August, 2005

JON W. DUDAS
*Director of the United States Patent and Trademark Office*